US010453158B2

(12) United States Patent
Lampropoulos et al.

(10) Patent No.: US 10,453,158 B2
(45) Date of Patent: Oct. 22, 2019

(54) SYSTEMS AND METHODS FOR PRODUCING MEDICAL DEVICES

(71) Applicant: Merit Medical Systems, Inc., South Jordan, UT (US)

(72) Inventors: Fred Lampropoulos, Salt Lake City, UT (US); Joseph Pierce, Cottonwood Heights, UT (US); Owen Xu, Sandy, UT (US); Jesse Velarde, West Jordan, UT (US); Kyle Knowles, Highland, UT (US); Justin Lampropoulos, Lehi, UT (US); Jesse Hansen, Sandy, UT (US); Nick Kapitula, Sandy, UT (US)

(73) Assignee: Merit Medical Systems, Inc., South Jordan, UT (US)

(*) Notice: Subject to any disclaimer, the term of this patent is extended or adjusted under 35 U.S.C. 154(b) by 302 days.

(21) Appl. No.: 15/293,556

(22) Filed: Oct. 14, 2016

(65) Prior Publication Data

US 2017/0109851 A1    Apr. 20, 2017

Related U.S. Application Data

(60) Provisional application No. 62/327,084, filed on Apr. 25, 2016, provisional application No. 62/243,379, filed on Oct. 19, 2015.

(51) Int. Cl.
G06Q 30/00 (2012.01)
G06Q 50/22 (2018.01)
G06Q 10/08 (2012.01)
G06Q 30/06 (2012.01)

(52) U.S. Cl.
CPC ......... *G06Q 50/22* (2013.01); *G06Q 10/0875* (2013.01); *G06Q 30/016* (2013.01); *G06Q 30/0601* (2013.01)

(58) Field of Classification Search
CPC ........................................ G06Q 30/0601–0645
See application file for complete search history.

(56) References Cited

U.S. PATENT DOCUMENTS

| 6,594,642 B1 | 7/2003 | Lemchen |
| 2004/0095375 A1 | 5/2004 | Burmester et al. |
| 2004/0181465 A1* | 9/2004 | Kan ........................ G06Q 30/02 705/26.5 |
| 2006/0100541 A1* | 5/2006 | Aparicio ................. B01L 3/545 600/562 |

(Continued)

FOREIGN PATENT DOCUMENTS

| CA | 2985789 | 2/2014 |
| WO | 2003096154 | 11/2003 |
| WO | 2009157613 | 12/2009 |

OTHER PUBLICATIONS

Freitas, Robert A., Jr. (Jan. 2010). The future of nanomedicine. The Futurist, 44, 21-22. Retrieved from https://search.proquest.com/do (Year: 2010).*

(Continued)

*Primary Examiner* — Resha Desai
*Assistant Examiner* — Ashley D Preston
(74) *Attorney, Agent, or Firm* — Stoel Rives LLP

(57) ABSTRACT

The present disclosure provides systems and methods for producing customized medical devices, such as customized medical grade labels, customized medical kits, and other medical devices having customizable features.

21 Claims, 19 Drawing Sheets

(56) References Cited

U.S. PATENT DOCUMENTS

| | | | |
|---|---|---|---|
| 2006/0167577 A1* | 7/2006 | Clark | G06F 8/71 |
| | | | 700/97 |
| 2007/0233049 A1 | 10/2007 | Wehba et al. | |
| 2007/0250830 A1 | 10/2007 | Holmberg et al. | |
| 2010/0239821 A1 | 9/2010 | Nagao et al. | |
| 2013/0218589 A1 | 8/2013 | Lerner | |
| 2014/0046787 A1 | 2/2014 | Norman et al. | |
| 2014/0263674 A1* | 9/2014 | Cerveny | G06K 19/06028 |
| | | | 235/494 |
| 2014/0277659 A1* | 9/2014 | Kumar | G05B 19/4097 |
| | | | 700/97 |
| 2015/0242713 A1* | 8/2015 | Hoover | G06F 3/1243 |
| | | | 358/1.6 |

OTHER PUBLICATIONS

International Search Report and Written Opinion dated Feb. 3, 2017 for PCT/US2016/057125.
European Search Report dated Mar. 26, 2019 for EP16858028.0.

* cited by examiner

FIG. 9

| 7200 | | | 10:55 PM Sets By Customer | | 8% ⊂⊃, + |
|---|---|---|---|---|---|
| Group (7200) | Me | | Mar 11, 2016, 3:32 PM | 6 Label Sets | |
| Merit (1234) | Jesse<br>Engineer | | Mar 15, 2016, 9:34 AM | 4 Label Sets | |
| Oscher (7116) | Me<br>You | | Mar 14, 2016, 10:20 AM | 5 Label Sets | |
| S | S<br>S | | Apr 1, 2016, 2:36 PM | 1 Label Set | |

FIG. 12

SYSTEMS AND METHODS FOR PRODUCING MEDICAL DEVICES

RELATED APPLICATIONS

This application claims priority to U.S. Provisional Application No. 62/243,379, filed on Oct. 19, 2015, and titled, "Systems and Methods for Producing Medical Devices," and U.S. Provisional Application No. 62/327,084, filed on Apr. 25, 2016, and titled, "Systems and Methods for Producing Medical Devices," both of which are hereby incorporated herein by reference in their entireties.

COPYRIGHT NOTICE

© 2016 Merit Medical Systems, Inc. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 C.F.R. § 1.71(d).

TECHNICAL FIELD

The present disclosure is directed to systems and methods for producing medical devices, and more particularly to systems and methods for producing customized medical devices.

BRIEF DESCRIPTION OF THE DRAWINGS

Additional aspects and advantages will be apparent from the following detailed description of preferred embodiments, which proceeds with reference to the accompanying drawings, in which:

FIG. 9 is another user interface of a medical device customization client computing device, according to one embodiment.

FIG. 12 is another user interface of a medical device customization client computing device, according to one embodiment.

DETAILED DESCRIPTION

The present disclosure will be better understood from the detailed description provided below and from the drawings of various embodiments, methods, and examples herein. These specifics, however, are provided for explanatory purposes that help the various embodiments of the disclosure to be better understood. The invention should therefore not be limited by the described embodiments, methods, and examples, but by all embodiments and methods within the scope and spirit of the invention as claimed.

The present disclosure provides systems and methods for generating customized medical devices, such as medical grade labels, customized medical kits, and other medical devices having customizable features. The disclosed embodiments enable customer approval of a visualization (e.g., a WYSWYG rendering) of the customized medical device, which evokes automated processes for preparing manufacturing documentation and order generation.

The features of the systems and methods will now be described with reference to the drawings summarized above. Throughout the drawings, reference numbers are reused to indicate correspondence between referenced elements. In addition, the first digit of each reference number indicates the figure in which the element first appears. The drawings, associated descriptions, and specific implementation are provided to illustrate embodiments of the invention, and not to limit the scope of the invention. The scope of the invention is defined by the appended claims.

Figure 1:
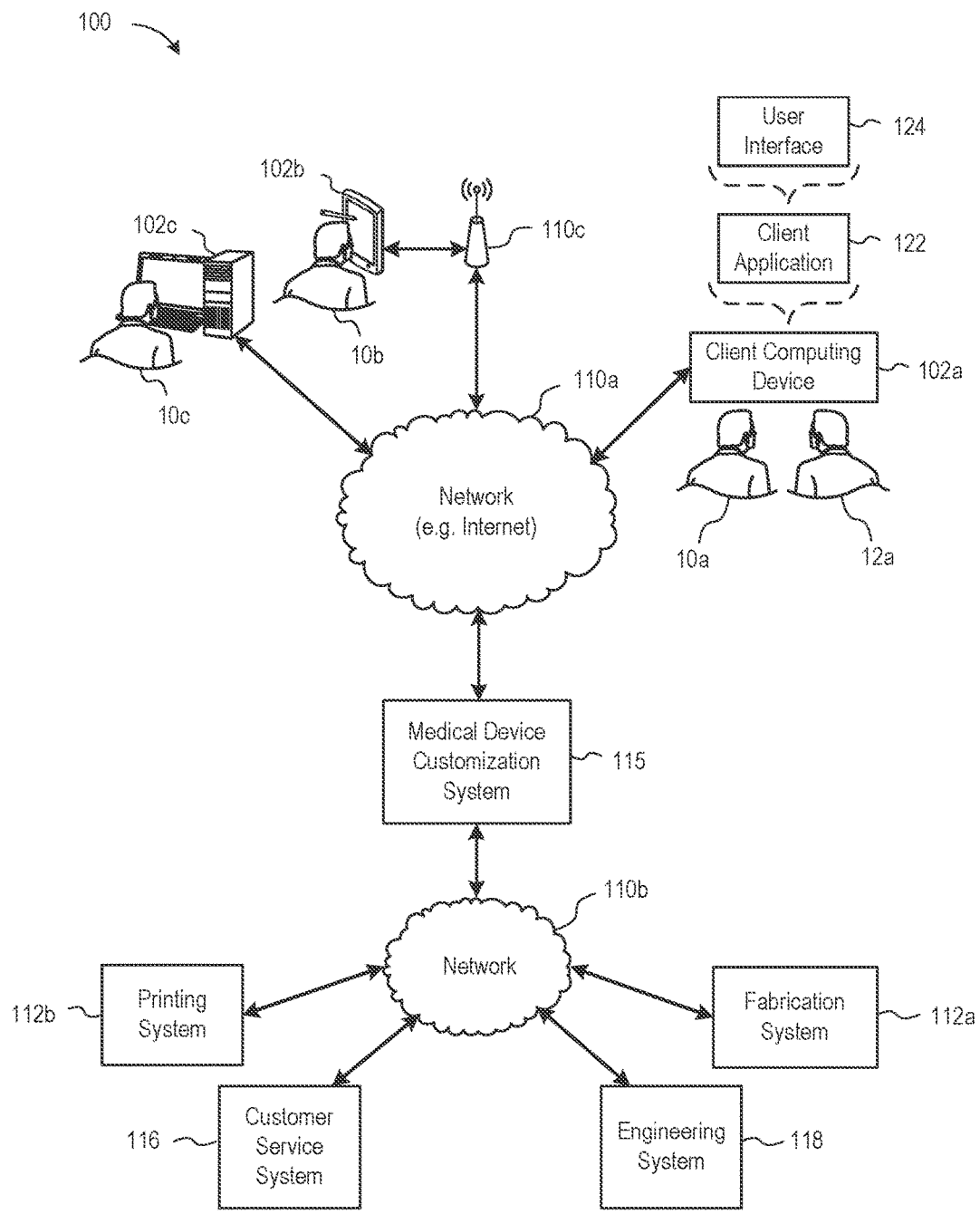
FIG. 1 is a system for producing customized medical devices, according to one embodiment of the present disclosure.

FIG. 1 is a system 100 for producing customized medical devices according to one embodiment. The system 100 enables design and production of customized medical devices, such as customized medical grade labels, customized medical kits, and other medical devices having customizable features. The system 100 may include a plurality of medical device customization client computing devices 102a, 102b, 102c (individually and collectively 102) coupled to a medical device customization system 115 over a communication network 110a (e.g., the Internet).

Each client computing device 102 provides an interface for a salesperson 10a, 10b, 10c (individually and collectively 10) and/or a customer 12a to design a customized medical device for manufacture. The interface may be provided by a client application 122 presenting a user interface 124 on a display of the client computing device 102. The client computing device 102 can prepare a specification file that specifies a medical device and customization of one or more features of the medical device to produce a customized medical device. The client computing device 102 communicates the specification file to the medical device customization system 115 via a communication network 110a (e.g., a public communication network such as the Internet or a wireless telephone network). The client computing device 102 may be a mobile computing device such as a laptop, a smartphone, a tablet, a wearable device (e.g., watch, augmented reality glasses), or may be any other suitable computing device (e.g., a desktop computer).

Figure 2:
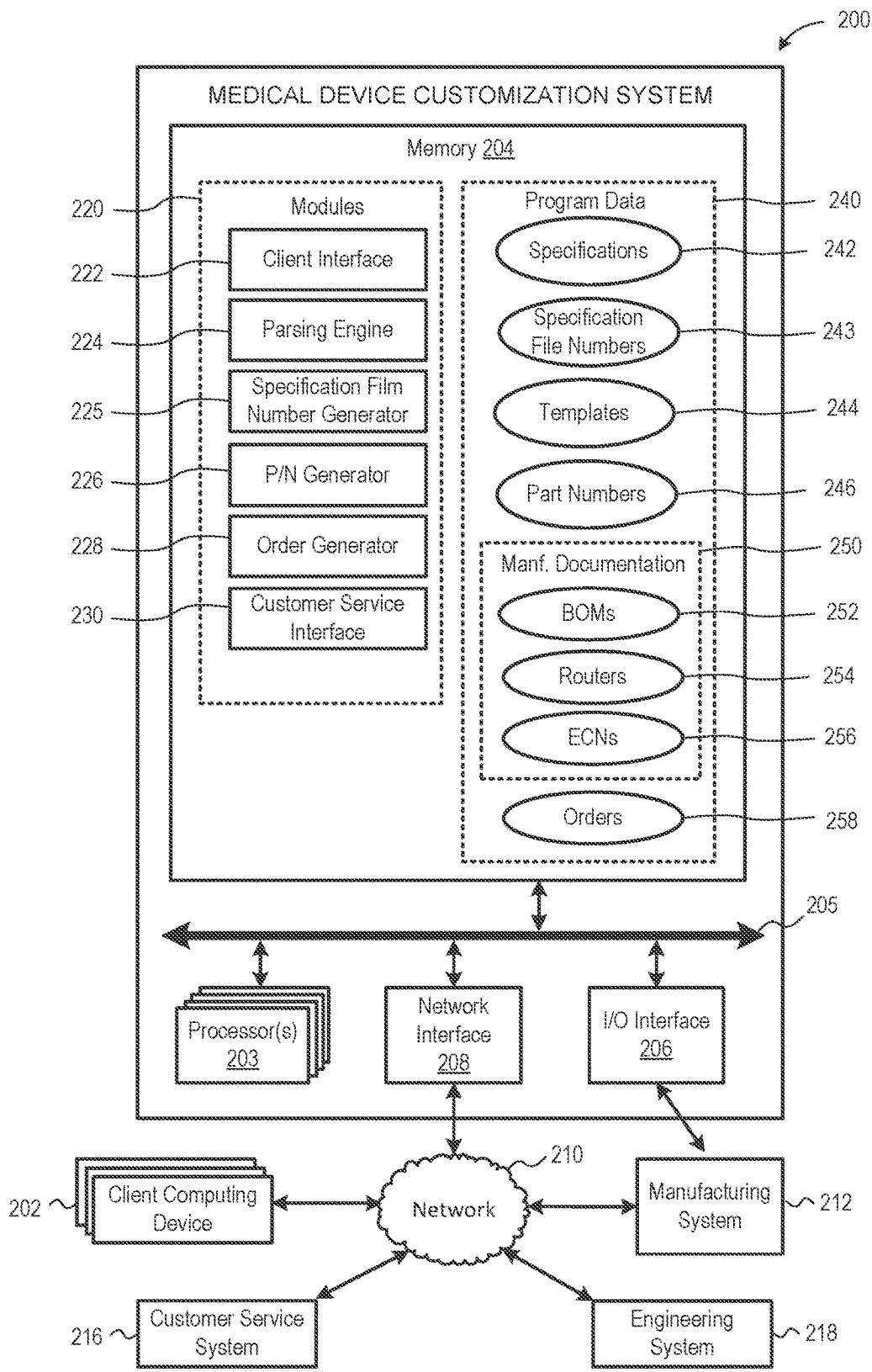
FIG. 2 is a medical device customization system, according to one embodiment.

The medical device customization system 115 receives the specification file from the client computing device 102. The medical device customization system 115 uses the specification file to generate an order to produce the customized medical device according to the specifications provided in the specification file, and to provide the order to a fabrication system 112*a* and/or a printing system 112*b* (individually and collectively a manufacturing system 112). The medical device customization system 115 provides and receives electronic communications to/from one or more other systems, such as the manufacturing system(s) 112, a customer service system 116, and/or an engineering system 118. The medical device customization system 115 receives and transmits these electronic communications over a network 110*b*, which may be the same as the network 110*a* from which the specification file is received or may be a private network, such as local area network (LAN). The communication networks 110*a*, 110*b* may include a wireless network 110*c* and may be collectively referred to as a network 110. A medical device customization system 115, according to one embodiment, is shown in FIG. 2 and discussed below with reference to the same.

The manufacturing systems 112, including the fabrication system 112*a* and the printing system 112*b*, provide capabilities to produce a customized medical device, such as customized medical grade labels, customized medical kits, and other medical devices having customizable features. The manufacturing system 112 may be internal or local to the medical device customization system 115 (e.g., at the same facility, at the same company, or on the same LAN), or may be a remote third-party system (e.g., a contracted manufacturing facility). The manufacturing systems 112 may be automated, manual (involving one or more human-performed functions), or a combination thereof.

The engineering system 118 may provide an approval function to ensure compliance of the customized medical device with quality, safety, and similar requirements or expectations. The approval function may be automated (e.g., based on collecting and processing sensor data), manual (involving one or more human-performed functions), or a combination thereof.

The customer service system 116 may provide inputs and approvals to a production process as orchestrated by the medical device customization system 115. For example, the customer service system 116 may shepherd the generating and/or assigning of a product number for the customized medical device.

FIG. 2 is a medical device customization system 200, according to one embodiment. The medical device customization system 200 may be the same as, similar to, or analogous to the medical device customization system 115 of FIG. 1. The system 200 may include one or more processors 203, a memory 204, an input/output interface 206, a network interface 208, and a system bus 205.

The one or more processors 203 may include one or more general purpose devices, such as an Intel®, AMD®, or other standard microprocessor. The one or more processors 203 may include a special purpose processing device, such as an ASIC, SoC, SiP, FPGA, PAL, PLA, FPLA, PLD, or other customized or programmable device. The one or more processors 203 perform distributed (e.g., parallel) processing to execute or otherwise implement functionalities of the present embodiments. The one or more processors 203 may run a standard operating system and perform standard operating system functions. It is recognized that any standard operating system may be used, such as, for example, Microsoft® Windows®, Apple® MacOS®, Disk Operating System (DOS), UNIX, IRIX, Solaris, SunOS, FreeBSD, Linux®, ffiM® OS/2®, and so forth.

The memory 204 may include static RAM, dynamic RAM, flash memory, one or more flip-flops, ROM, CD-ROM, DVD, disk, tape, or magnetic, optical, or other computer storage media. The memory 204 may include a plurality of program modules 220 and program data 240.

The program modules 220 be implemented in hardware and/or software and may include or otherwise encompass all or portions of other elements of the system 200. The program modules 220 may run multiple operations, concurrently or in parallel, by or on the one or more processors 203. In some embodiments, portions of the disclosed modules, components, and/or facilities are embodied as executable instructions embodied in hardware or firmware, or stored on a non-transitory, machine-readable storage medium. The instructions may comprise computer program code and, when executed by a processor and/or computing device, cause the processor, computing device, and/or computing system to implement certain processing steps, procedures, and/or operations, as disclosed herein. The modules, components, and/or facilities disclosed herein may be implemented and/or embodied as a driver, a library, an interface, an API, FPGA configuration data, firmware (e.g., stored on an EEPROM), and/or the like. In some embodiments, portions of the modules, components, and/or facilities disclosed herein are embodied as machine components, such as general and/or application-specific devices, including, but not limited to: circuits, integrated circuits, processing components, interface components, hardware controller(s), storage controller(s), programmable hardware, FPGAs, ASICs, and/or the like. Accordingly, the modules disclosed herein may be referred to as controllers, layers, services, engines, facilities, drivers, circuits, and/or the like.

The memory 204 may also include program data 240. Data generated by the system 200, such as by the program modules 220 or other modules, may be stored on the memory 204, for example, as stored program data 240. The stored program data 240 may be organized as one or more databases. In certain embodiments, the program data 240 may be stored in a database system. The database system may reside within the memory 204. In other embodiments, the program data 240 may be remote, such as in a distributed computing and/or storage environment. For example, the program data 240 may be stored in a database system on a remote computing device.

The input/output interface 206 may facilitate interfacing with one or more input devices and/or one or more output devices/systems. The input device(s) may include a keyboard, mouse, touch screen, light pen, tablet, microphone, sensor, or other hardware with accompanying firmware and/or software. In the illustrated embodiment of FIG. 2, the output system may be a manufacturing system 212. The output system(s) may also include a monitor or other display, printer, speech or text synthesizer, switch, signal line, or other hardware with accompanying firmware and/or software.

The network interface 208 may facilitate communication with other computing devices and/or networks 210, such as the Internet and/or other computing and/or communications networks. The network interface 208 may be equipped with conventional network connectivity, such as, for example, Ethernet (IEEE 802.3), Token Ring (IEEE 802.5), Fiber Distributed Datalink Interface (FDDI), or Asynchronous Transfer Mode (ATM). Further, the computing device may be configured to support a variety of network protocols such as, for example, Internet Protocol (IP), Transfer Control Protocol (TCP), Network File System over UDP/TCP, Server Message Block (SMB), Microsoft® Common Internet File System (CIFS), Hypertext Transfer Protocols (HTTP), Direct Access File System (DAFS), File Transfer Protocol (FTP), Real-Time Publish Subscribe (RTPS), Open Systems Interconnection (OSI) protocols, Simple Mail Transfer Protocol (SMTP), Secure Shell (SSH), Secure Socket Layer (SSL), and so forth.

The system bus 205 may facilitate communication and/or interaction between the other components of the system 200, including the one or more processors 203, the memory 204, the input/output interface 206, and the network interface 208.

As noted, the system 200 also includes various program modules 220 (or engines, elements, or components) to implement functionalities of the system 200, including a client interface 222, a parsing engine 224, a specification file number generator 225, a product number generator 226, an order generator 228, and/or a customer service interface 230. These elements may be embodied, for example, at least partially in the program modules 220. In other embodiments, these elements may be embodied or otherwise implemented in hardware of the system 200. The system 200 also includes specifications 242 (e.g., specification files) for customized medical devices, specification file numbers 243 (e.g., artwork numbers), templates 244 for documentation forms or medical devices (e.g., a label template), part numbers 246 for customized medical devices, and manufacturing documentation 250 produced by the system 200 (which may comprise one or more manufacturing documents including bills of material 252 (BOMs), routers 254, and engineering change notices 256), and orders 258, all of which may be stored in the program data 240, which may be generated, accessed, and/or manipulated by the program modules 220.

The client interface 222 utilizes the one or more processors 203 and/or the network interface 208, to receive specifications 242 from a client computing device 202 over the electronic communication network 210. The specifications 242 may be received as a specification file. The client interface 222 may receive the specification file or specifications 242 via an email sent from a client application of a client computing device 202. In certain embodiments, the customized medical device is a set of customized medical grade labels. In certain embodiments, the customized medical device is a kit including a medical grade label that is biocompatible and a pen having ink that marks on the label and maintains integrity (e.g., does not smear or smudge) on the label in the presence of liquid (e.g., saline, contrast, or biological fluids). In certain embodiments, the customized medical device comprises a plurality of polymer components (e.g., as provided in a listing of materials of a BOM 252) assembled together using the instructions provided by a router 254 for assembling the customized medical device. The client interface 222 stores one or more of the specification file and the specifications 242 in the memory 204.

The parsing engine 224 may utilize the one or more processors 203 to parse a specification file received from the client computing device 202 to extract from the specification file the specifications 242 that specify the medical device and customization of the one or more features of the medical device to produce the customized medical device. The parsing engine 224 stores the specifications 242 to the memory 204.

The specification file number generator 225 may utilize the one or more processors 203 to generate a specification file number 243 for the specification file. In certain embodiments, the specification file number generator 225 is an artwork number generator to generate an artwork number for an artwork file received from the client computing device 202, such as to provide specifications 242 for a set of customized medical grade labels.

The part number generator 226 utilizes the one or more processors 203 to generate a part number 246 for the customized medical device. The part number 246 can be unique to the customized medical device. The part number 246 can be unique to a customer placing an order for the customized medical device.

Figure 3:
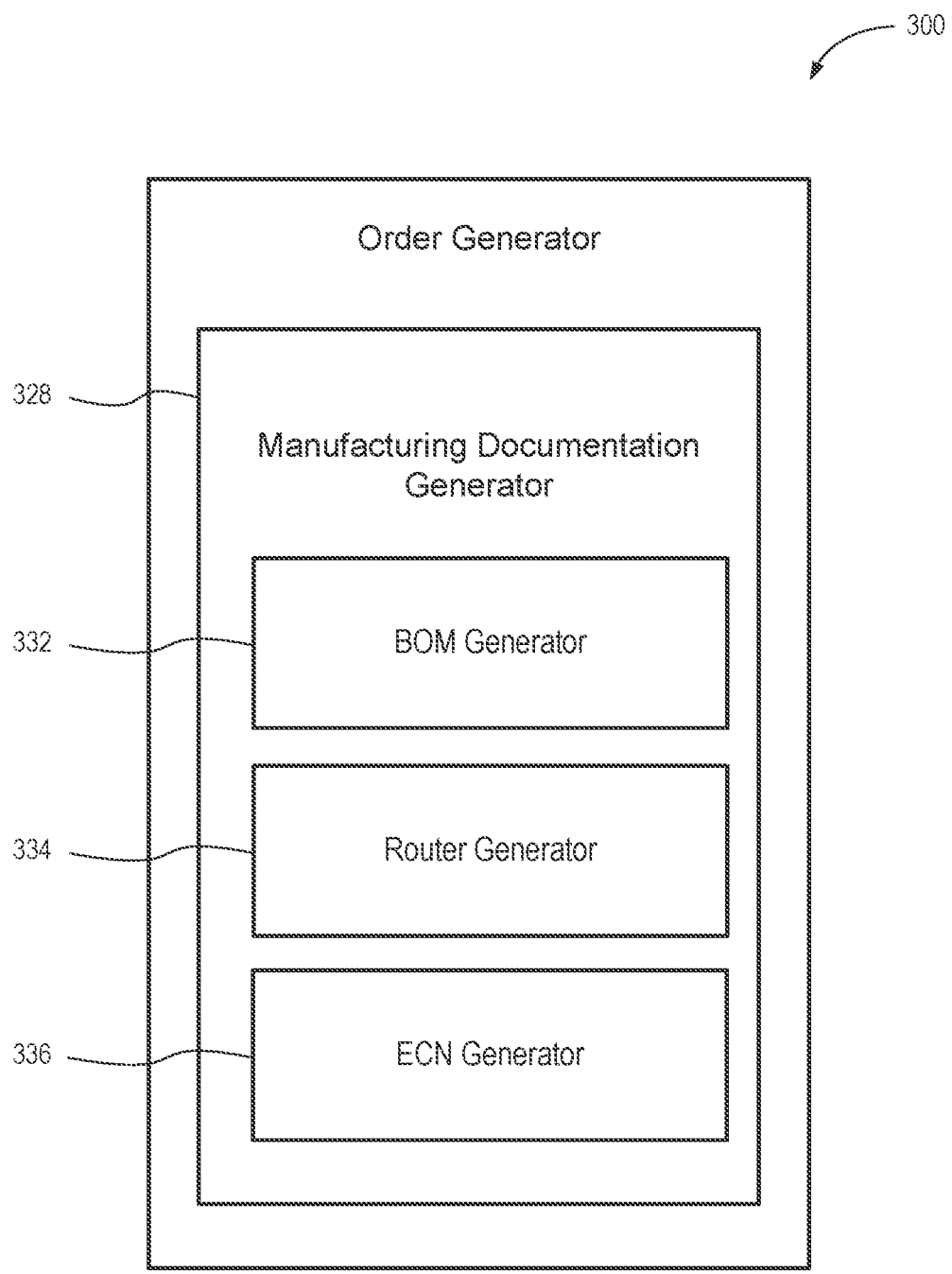
FIG. 3 is an order generator of a medical device customization system, according to one embodiment.

The order generator 228 utilizes the one or more processors 203 to generate a manufacturing order 258 to produce the customized medical device according to the specification file, and to provide the manufacturing order 258 to a manufacturing system 212. The manufacturing order 258 to produce the customized medical device may be a purchase order to be provided to a third-party manufacturing system 212. The manufacturing order 258 to produce the customized medical device may be a work order to be provided to an internal manufacturing system 212. The manufacturing order 258 can include one or more manufacturing documents 250. The manufacturing order 258 optionally may be provided to an engineering system 218 for review and/or approval to produce the manufacturing order 258. An example of the order generator 228 is depicted in FIG. 3 and described below with reference to the same.

The customer service interface 230 utilizes the one or more processors 203 to communicate a part number 246 to a customer service system 216. The part number 246 communicated may include one or more of a kit part number, an artwork part number, and an ECN part number.

The customer service system 216 may be provided this information in order to be able to communicate back to a sales rep who submitted the design (e.g., to receive any additional information (e.g., to receive the initial purchase order) prior to finalizing all of the automatically generated documentation (BOM, Artwork, etc.). Once all of the customer information is received, the customer service system 216 (e.g., by a customer service representative) may initiate an approval process. The customer service interface 230 may also provide an indication of additional processing steps to be performed.

The specifications 242 may be received as a specification file. The specifications 242 specify a medical device and customization of one or more features of the medical device to produce a customized medical device. In certain embodiments, the specifications 242 may be embodied as artwork (e.g., a graphical representation of, for example, a customized medical grade label or other customized medical device). Stated otherwise, the specification file may be an artwork file that provides a precise rendering of the customized medical device, such as a set of one or more medical grade labels. The specification file may be an extensible mark-up language (XML) file that includes elements defining the specifications 242 for the customized medical device. A specification file number 243 may be generated and stored to uniquely identify a set of specifications 242 or a specification file. The specifications 242 of, for example, a customized medical device in the form of a medical grade label may include label dimensions, label color, label transparency (or lack thereof, e.g., translucence, opaqueness), text, text font, text color, text size, text formatting (e.g., indentation, number of lines of text), text styling (e.g., bold, italic, underline), and label graphics.

The templates 244 may include templates for documentation forms (e.g., manufacturing documentation 250) or medical devices (e.g., a label template).

The part numbers 246 are each generated and stored to uniquely identify a customized medical device. Each part number 246 can also be unique to a customer purchasing the customized medical device.

The manufacturing documentation 250 produced by the system 200 is documentation to enable manufacture of the customized medical device. For example, the manufacturing documentation 250 may include one or more of a bill of material (BOM) 252, a router 254, and an engineering change notice (ECN) 256.

The BOM 252 is generated based on the specifications 242 or a specification file. The BOM 252 provides a listing of materials to produce the customized medical device. For example, for a customized medical grade label, the BOM 252 may include a listing of materials such as paper/film, ink, and/or adhesive. For a medical device apparatus, such as may be manufactured of a plurality of components, the BOM 252 may include a listing of materials to manufacture each of the components (e.g., polymers, molds, fasteners, adhesive, etc.).

The router 254 is generated based on one or more of the specifications 242 and the BOM 252, and provides instructions for manufacturing or otherwise producing the customized medical device. The router 254 may provide locations or stations for performing steps of the production. The router 254 may specify equipment and equipment settings or configurations to perform steps of the instructions. The router 254 may be generated based on a template 244 and/or may be otherwise generated to be compatible with a destination manufacturing system 212.

The ECN 256 is generated to associate one or more of a part number 246, a set of specifications 242 or specification file, a BOM 252, and a router 254. The ECN 256 may be configured according to a template 244. The ECN 256 may be communicated to the engineering system 218, which may include an automated process or to a manual process to enable engineering or similar review of the manufacturing documentation 250 generated to produce the manufacturing order 258.

In certain embodiments, the medical device customization system 200 may determine, based on the specification file, whether the customized medical device is a new customization or a revision of an existing customization. If the customized medical device is a revision of an existing customization, the manufacturing order 258 to produce the customized medical device may be transmitted to a manual manufacturing system 212. If the customized medical device is a new customization, the manufacturing order 258 to produce the customized medical device may be transmitted to an automated manufacturing system 212.

FIG. 3 is an order generator 300 of a medical device customization system, according to one embodiment. The order generator 300 may be the same as, similar to, or analogous to the order generator 228 of FIG. 2. The order generator 300 may include or otherwise utilize one or more processors (e.g., the one or more processors 203 of FIG. 2) to generate a manufacturing order to produce the customized medical device according to a specification file. The order generator 300 also provides the order to a manufacturing system (e.g., a manufacturing system 212 of FIG. 2). The order generator 300 includes a manufacturing documentation generator 328, which may include a BOM generator 332, a router generator 334, and an ECN generator 336. The order generator 300 produces a manufacturing order that includes one or more manufacturing documents.

The manufacturing documentation generator 328 utilizes one or more processors to generate manufacturing documentation, which may include one or more manufacturing documents, to enable a manufacturing system to produce the customized medical device according to the specification file. The order generator 300 generates the manufacturing order based on or to include the one or more manufacturing documents.

The BOM generator 332 utilizes one or more processors to generate a bill of materials (BOM) based on the specification file. The BOM generator 332 generates the BOM to provide a listing of materials to produce the customized medical device.

The router generator 334 utilizes one or more processors to generate a router based on the BOM and the specification file. The router generator 334 generates the router to provide instructions for assembling or otherwise producing the customized medical device.

The ECN generator 336 utilizes one or more processors to generate an ECN to associate the specification file, the BOM, and the router. The ECN generator 336 may also provide the ECN, the specification file, the BOM, and the router to an engineering system for review and approval to produce the manufacturing order.

Figure 4:
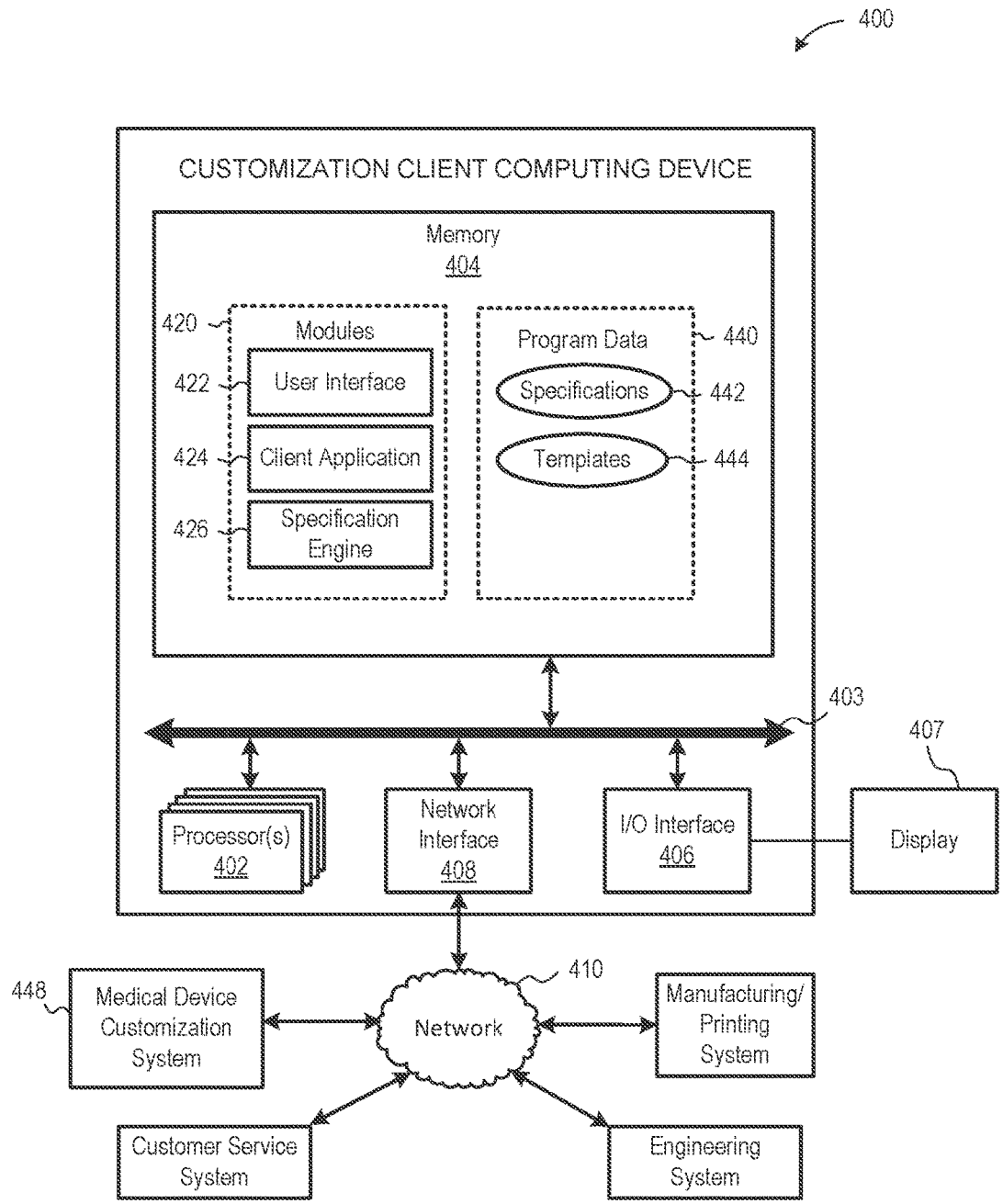
FIG. 4 is a medical device customization client computing device, according to one embodiment.

FIG. 4 is a medical device customization client computing device 400, according to one embodiment. The medical device customization client computing device 400 runs on a client computing device that may be the same as, similar to, or analogous to the client computing device 102 of FIG. 1 and/or the client computing device 202 of FIG. 2. The client computing device 400 may include one or more processors 402, a memory 404, an input/output interface 406, a network interface 408, and a device bus 403.

The one or more processors 402 may include one or more general purpose devices, such as an Intel®, AMD®, or other standard microprocessor. The one or more processors 203 may include a special purpose processing device, such as an ASIC, SoC, SiP, FPGA, PAL, PLA, FPLA, PLD, or other customized or programmable device. The one or more processors 402 may perform distributed (e.g., parallel) processing to execute or otherwise implement functionalities of the present embodiments. The one or more processors 402 may run a standard operating system and perform standard operating system functions. It is recognized that any standard operating systems may be used, such as, for example, Microsoft® Windows®, Apple® MacOS®, Disk Operating System (DOS), UNIX, IRIX, Solaris, SunOS, FreeBSD, Linux®, ffiM® OS/2®, and so forth.

The memory 404 may include static RAM, dynamic RAM, flash memory, one or more flip-flops, ROM, CD-ROM, DVD, disk, tape, or magnetic, optical, or other computer storage media. The memory 404 may include a plurality of program modules 420 and program data 440.

The program modules 420 may include all or portions of other elements of the client computing device 400. The program modules 420 may run multiple operations, concurrently or in parallel, by or on the one or more processors 402. In some embodiments, portions of the disclosed modules, components, and/or facilities are embodied as executable instructions embodied in hardware or firmware, or stored on a non-transitory, machine-readable storage medium. The instructions may comprise computer program code and, when executed by a processor and/or a computing device, cause the processor, computing device, and/or a computing system to implement certain processing steps, procedures, and/or operations, as disclosed herein. The modules, components, and/or facilities disclosed herein may be implemented and/or embodied as a driver, a library, an interface, an API, FPGA configuration data, firmware (e.g., stored on an EEPROM), and/or the like. In some embodiments, portions of the modules, components, and/or facilities disclosed herein are embodied as machine components, such as general and/or application-specific devices, including, but not limited to: circuits, integrated circuits, processing components, interface components, hardware controller(s), storage controller(s), programmable hardware, FPGAs, ASICs, and/or the like. Accordingly, the modules disclosed herein may be referred to as controllers, layers, services, engines, facilities, drivers, circuits, and/or the like.

The memory 404 may also include program data 440. Data generated by the client computing device 400, such as by the program modules 420 or other modules, may be stored on the memory 404, for example, as stored program data 440. The stored program data 440 may be organized as one or more databases. In certain embodiments, the program data 440 may be stored in a database system. The database system may reside within the memory 404. In other embodiments, the program data 440 may be remote, such as in a distributed computing and/or storage environment. For example, the program data 440 may be stored in a database system on a remote computing device.

The input/output interface 406 may facilitate interfacing with one or more input devices and/or one or more output devices/systems. The input device(s) may include a keyboard, mouse, touch screen, light pen, tablet, microphone, sensor, or other hardware with accompanying firmware and/or software. The output system(s) may also include a monitor or other display 407 (e.g., a touchscreen), printer, speech or text synthesizer, switch, signal line, or other hardware with accompanying firmware and/or software.

The network interface 408 may facilitate communication with other computing devices and/or networks 410, such as the Internet and/or other computing and/or communications networks. The network interface 408 may be equipped with conventional network connectivity, such as, for example, Ethernet (IEEE 802.3), Token Ring (IEEE 802.5), Fiber Distributed Datalink Interface (FDDI), or Asynchronous Transfer Mode (ATM). Further, the network interface 408 may be configured to support a variety of network protocols such as, for example, Internet Protocol (IP), Transfer Control Protocol (TCP), Network File System over UDP/TCP, Server Message Block (SMB), Microsoft® Common Internet File System (CIFS), Hypertext Transfer Protocols (HTTP), Direct Access File System (DAFS), File Transfer Protocol (FTP), Real-Time Publish Subscribe (RTPS), Open Systems Interconnection (OSI) protocols, Simple Mail Transfer Protocol (SMTP), Secure Shell (SSH), Secure Socket Layer (SSL), and so forth.

The device bus 403 may facilitate communication and/or interaction between the other components of the client computing device 400, including the one or more processors 402, the memory 404, the input/output interface 406, and the network interface 408.

As noted, the client computing device 400 also includes various program modules 420 (or engines, elements, or components) to implement functionalities of the client computing device 400, including a user interface 422, a client application 424, and a specification engine 426. These elements may be embodied, for example, at least partially in the program modules 420. In other embodiments, these elements may be embodied or otherwise implemented in hardware of the client computing device 400. The client computing device 400 also includes specifications 442 (e.g., specification files) for customized medical devices and templates 444 for documentation forms or medical devices (e.g., label templates). The user interface 422 may be provided by the client application 424 to be presented on a display 407 of the client computing device 400. The client application 424 on the client computing device 400 may enable a user (e.g., a sales rep or customer) to design a customized medical device, presenting a rendering of the customized medical device in a what-you-see-is-what-you-get (WYSIWYG) fashion. The specification engine 426 generates specifications 442 or a specification file to transmit to a medical device customization system 448 (such as the medical device customization system 200 of FIG. 2) for processing. One or more of the templates 444 may be used to generate the specification file and/or a rendering of the customized medical device in the user interface 422 on the display 407.

Figure 5A:
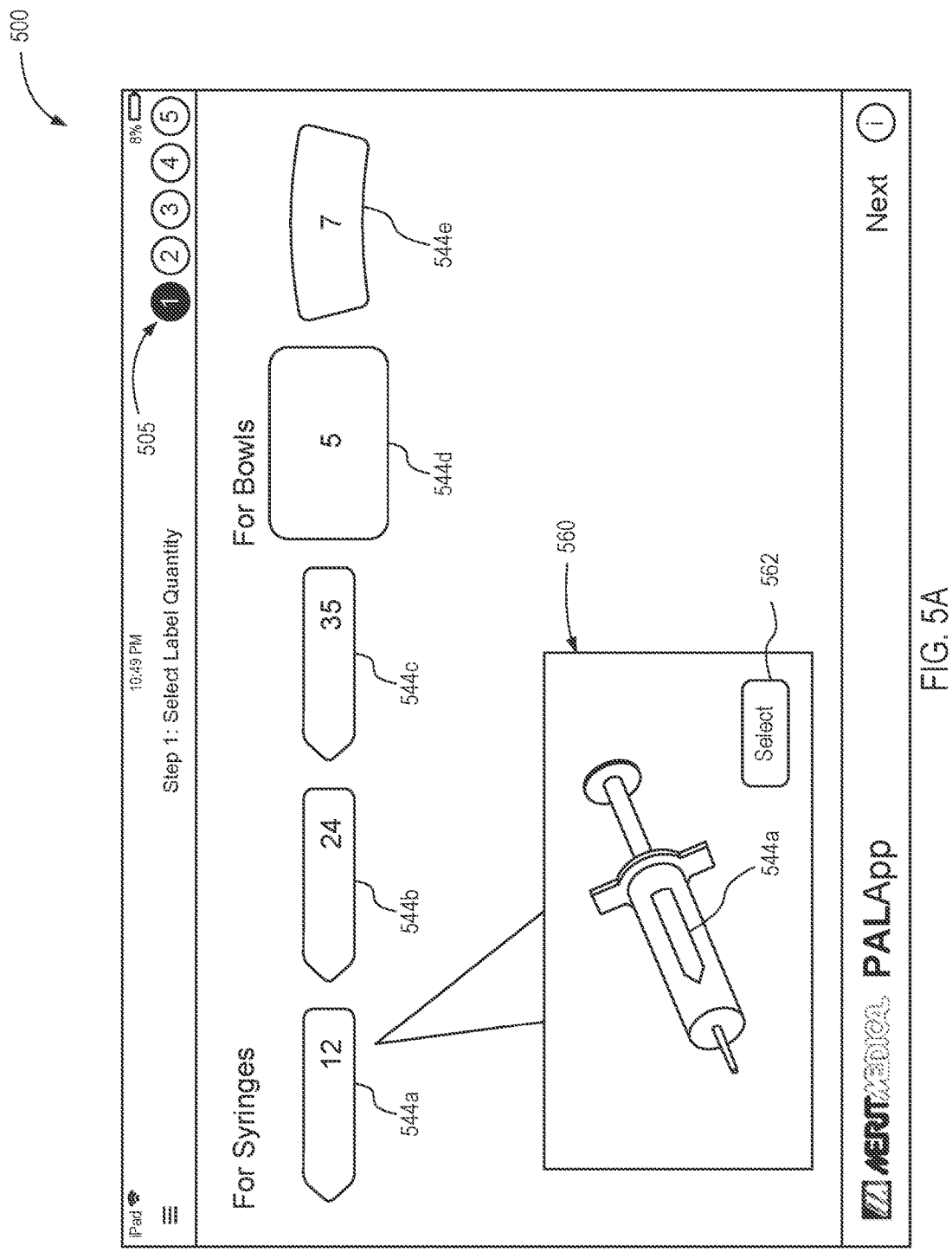
FIGS. 5A and 5B are a user interface of a medical device customization client computing device, according to one embodiment.
Figure 5B:
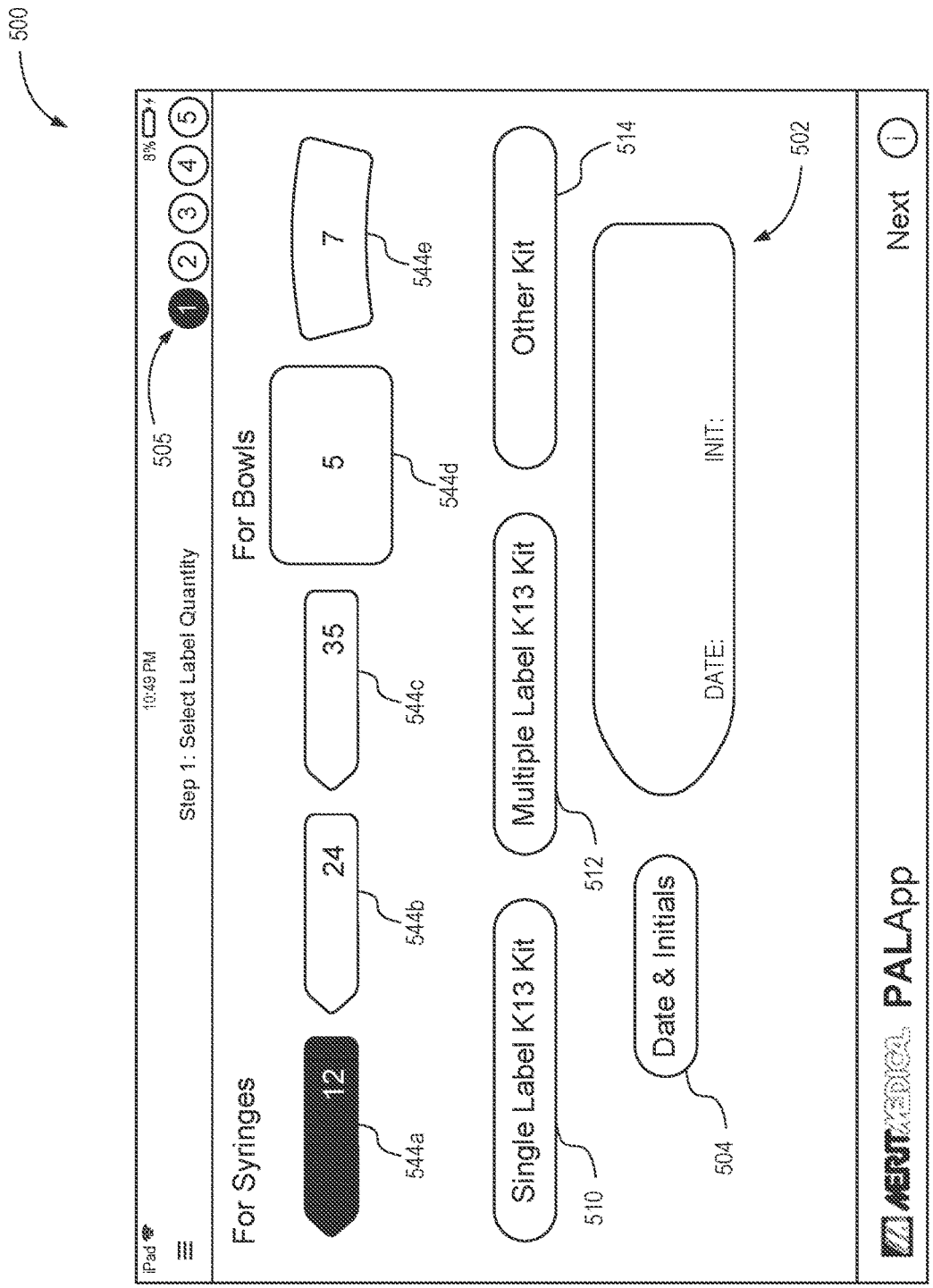

FIGS. 5A and 5B are a user interface 500 of a medical device customization client computing device, according to one embodiment. A plurality of label templates 544a, 544b, 544c, 544d, 544e (collectively 544) are presented for user selection. The label templates 544 may dictate a quantity of labels to be ordered by the customer. In FIG. 5A, as a user hovers over or otherwise selects one of the label templates 544, a rendering 560 may appear to portray context, such as how a resulting customized medical grade label would appear in use. In this case, the resulting customized medical grade label corresponding to the selected template is portrayed in context for comparison and to show interaction with a syringe. The rendering shows the label template 544a as it would appear on the syringe, which provides contextual information (e.g., relative sizing and positioning of the label compared to the syringe). A selection input component 562 may enable a user to select the corresponding label template.

Upon selection of a label template 544, input components for selecting options for a customized kit are presented, as shown in FIG. 5B, including a "single label kit" option input component 510, a "multiple label kit" option input component 512, and an "other kit" option input component 514. The single label kit option input component 510 would enable input selecting a kit with a quantity of a single label type. The multiple label kit option input component 512 would enable input selecting a kit with quantities of multiple label types. The other kit option input component 514 would enable input selecting a customized set of components in addition to a customized medical grade label resulting from the selected template 544. Also a rendering 502 of a label is presented and an input component 504 is presented to provide an option to insert pre-configured text into the label(s). The user interface 500 also provides a progress indicator 550 to show progress in a process of designing and/or ordering a customized medical device.

Figure 6:
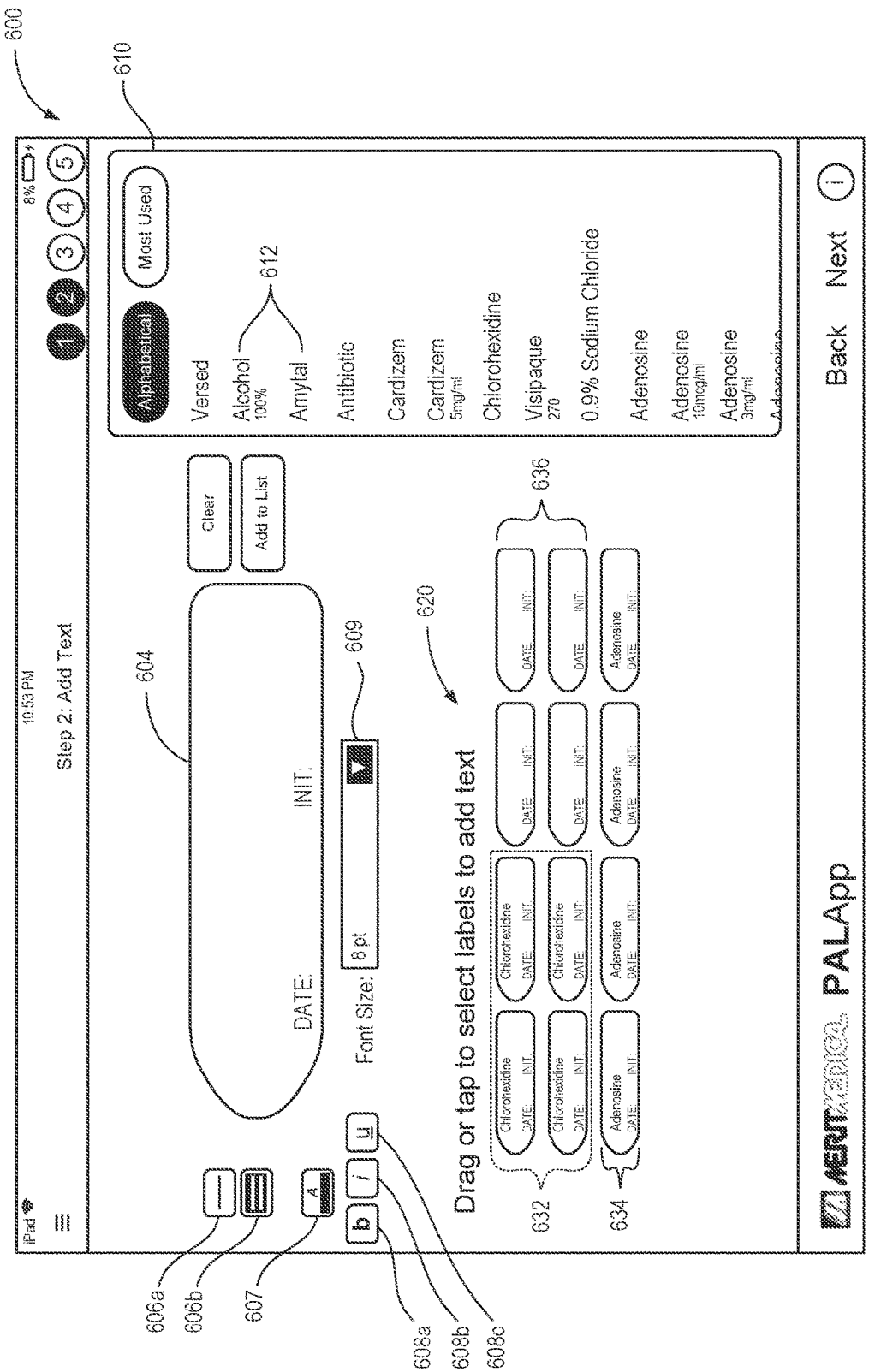
FIG. 6 is another user interface of a medical device customization client computing device, according to one embodiment.

FIG. 6 is another user interface 600 of a medical device customization client computing device, according to one embodiment. A rendering 604 of a label is presented (e.g., based on the earlier selection of a template), and one or more formatting input components 606a, 606b are presented to provide option input to select formatting options that configure specifications of the label, such as an option for a single line of text 606a, an option for multiple lines of text 606b, a font color option 607, font styling options (bold 608a, italic 608b, underline 608c), and a font size option 609. A listing 610 of preconfigured text options 612 may enable insertion of pre-configured text into the label template. A label selection tool 620 enables a user to select a set of one or more labels from a total quantity of labels provided by the template. The label selection tool 620 may allow a user to drag, tap, or otherwise select one or more labels in any arrangement for determining formatting and inserting pre-configured text options 612. In other words, a first set of labels 632 may be configured differently than a second set of labels 634 and/or a third set of labels 636. FIG. 6 illustrates the first set of labels 632 with pre-configured text "Chlorohexidine" included and the second set of labels 634 with pre-configured text "Adenosine" included. The third set of labels 636 remains without additional pre-configured text. In FIG. 6, a cursor has been dragged to create a box selecting the first set of labels 632. The second set of labels 634 was previously selected and formatted and/or configured. The third set of labels 636 remains unselected.

Figure 7:
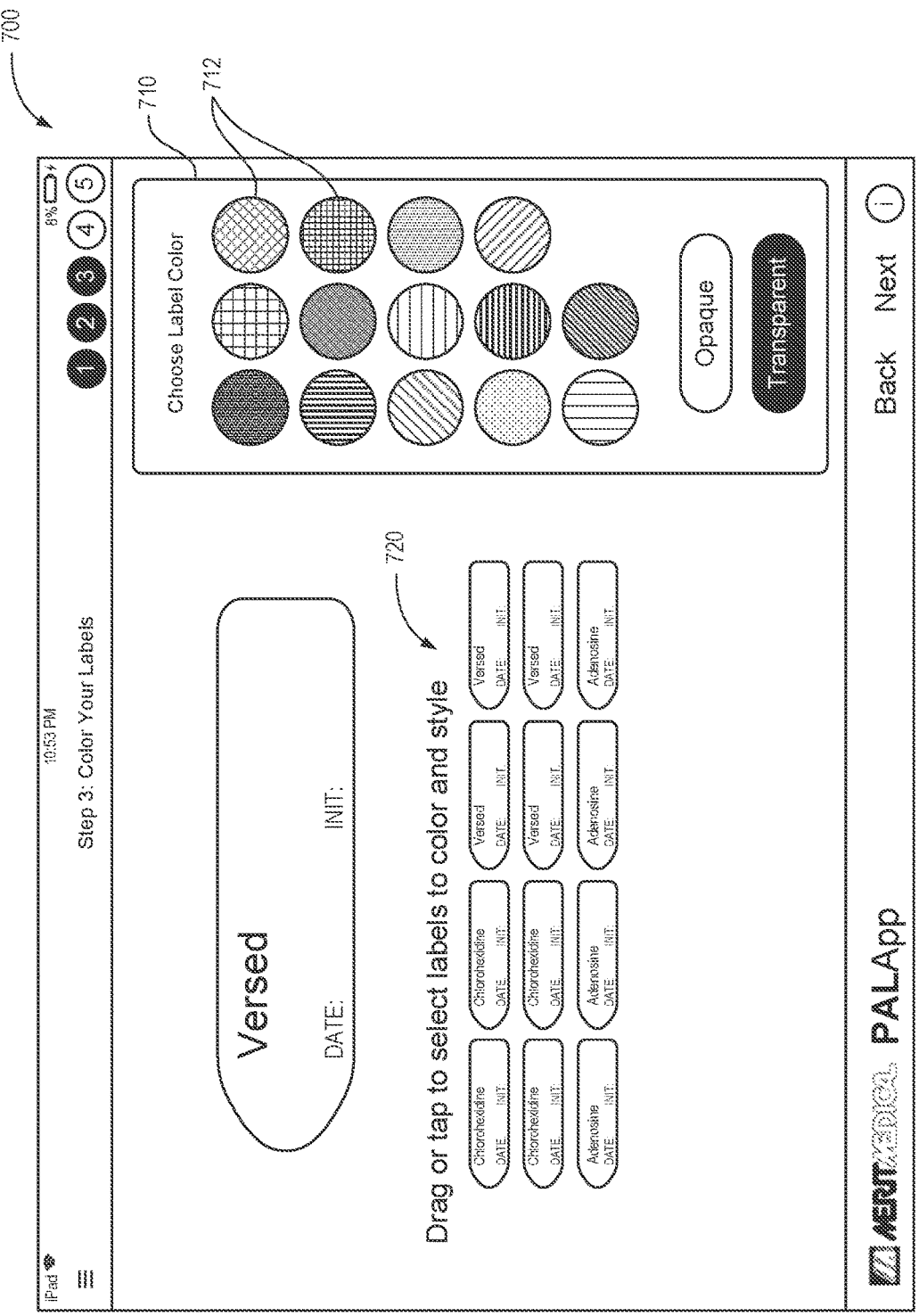
FIG. 7 is another user interface of a medical device customization client computing device, according to one embodiment.

FIG. 7 is another user interface 700 of a medical device customization client computing device, according to one embodiment. The user interface 700 provides a label selection tool 720 and a palette 710 that provides a plurality of colors/patterns 712 for coloring and/or patterning the labels. The label selection tool 720 may allow a user to drag, tap, or otherwise select one or more labels in any arrangement for determining colors and/or patterns 712. In other words, a first set of labels may be colored and/or patterned differently than a second set of labels and/or a third set of labels. Selecting a set of one or more labels using the label selection tool 720 and then selecting a color/pattern 712 from the palette 710 will accordingly configure the selected set of labels with the selected color/pattern 712.

Figure 8A:
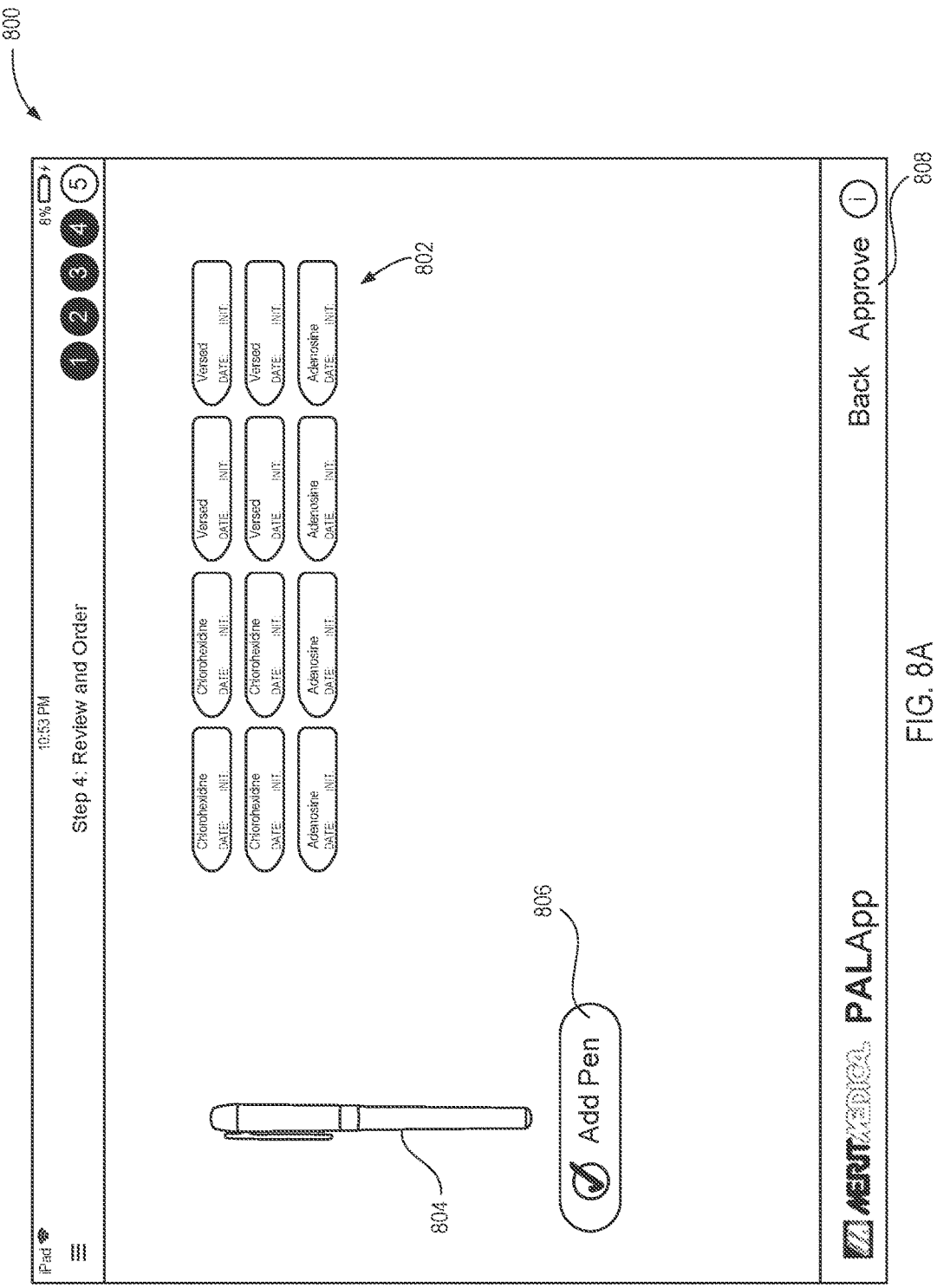
FIGS. 8A and 8B are another user interface of a medical device customization client computing device, according to one embodiment.
Figure 8B:

FIGS. 8A and 8B are another user interface 800 of a medical device customization client computing device, according to one embodiment. The user interface 800 provides a WYSIWYG rendering 802 of a customized medical device, in this case a set of medical grade labels, for approval by a user. The user interface 800 also includes an input component 806 for adding an add-on to the customized medical device. In this case, the add-on is a pen, for which a rendering 804 of the pen is also provided on the user interface 800. Upon manipulation of an approval navigation component 808, a signature area 807 may be presented, as shown in FIG. 8B, for providing final approval of the customized medical device. The signature and/or corresponding approval may be submitted or otherwise recorded by manipulation of an approval input component 809.

Figure 9:
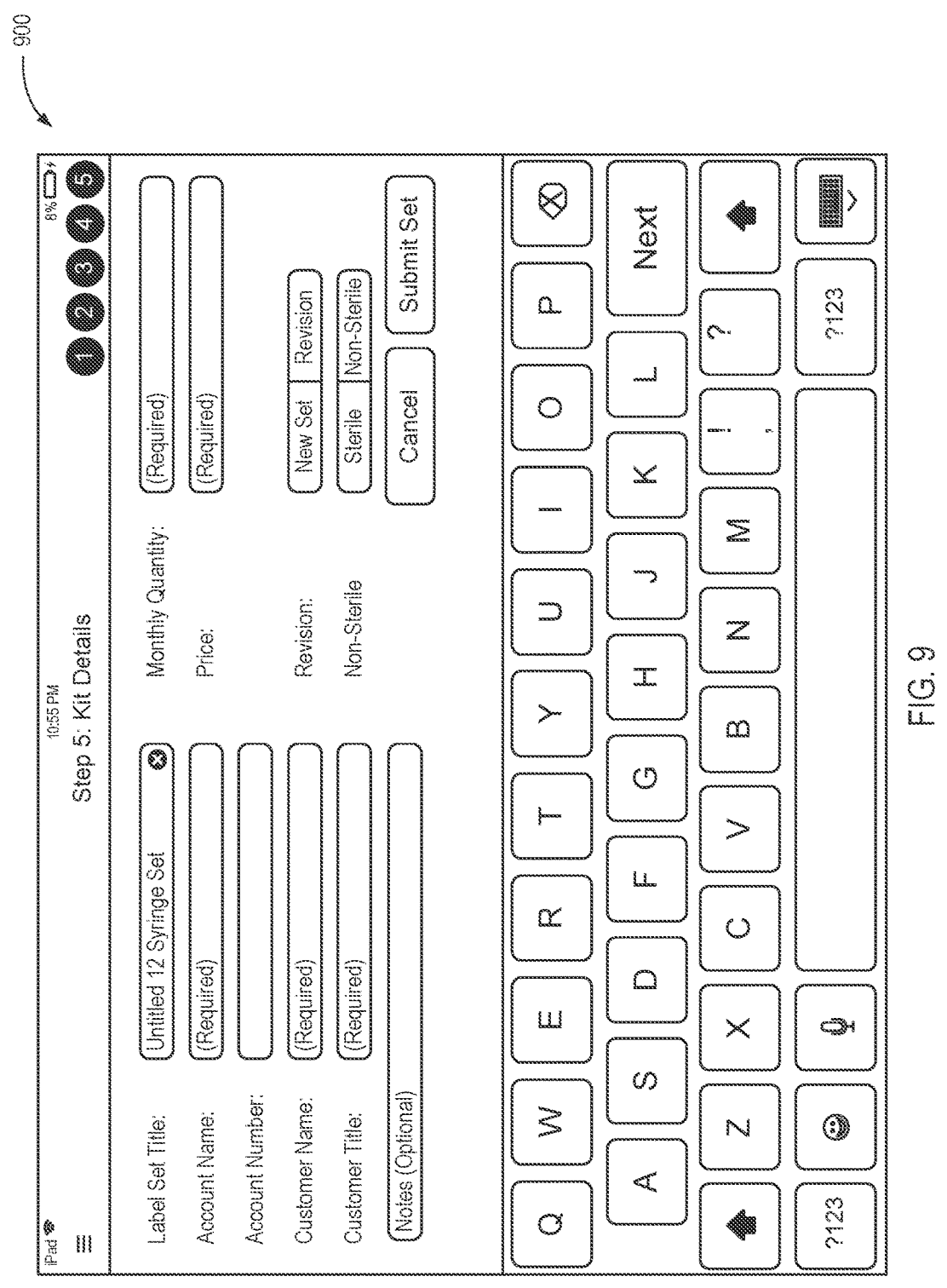

FIG. 9 is another user interface 900 of a medical device customization client computing device, according to one embodiment. The user interface 900 may allow user input of details of the customized medical device and/or order of the same. Upon approval (e.g., manipulation of the approval input component 809) and/or submission of the details of the customer order, a client application may gather the input data for processing by a specification engine. The specification engine may generate one or more specifications and/or specification files for transmittal to a medical device customization system. The input data may include one or more of a title, an account name, an account number, a customer name, a customer title, a monthly quantity, a price, and notes. Input components may also be provided for indicating whether the customized medical device is new or a revision of a previous customization and whether the customized medical device is sterile or non-sterile. A touch keyboard may be presented for providing text input.

Figure 10A:
FIGS. 10A and 10B are another user interface of a medical device customization client computing device, according to one embodiment.
Figure 10B:
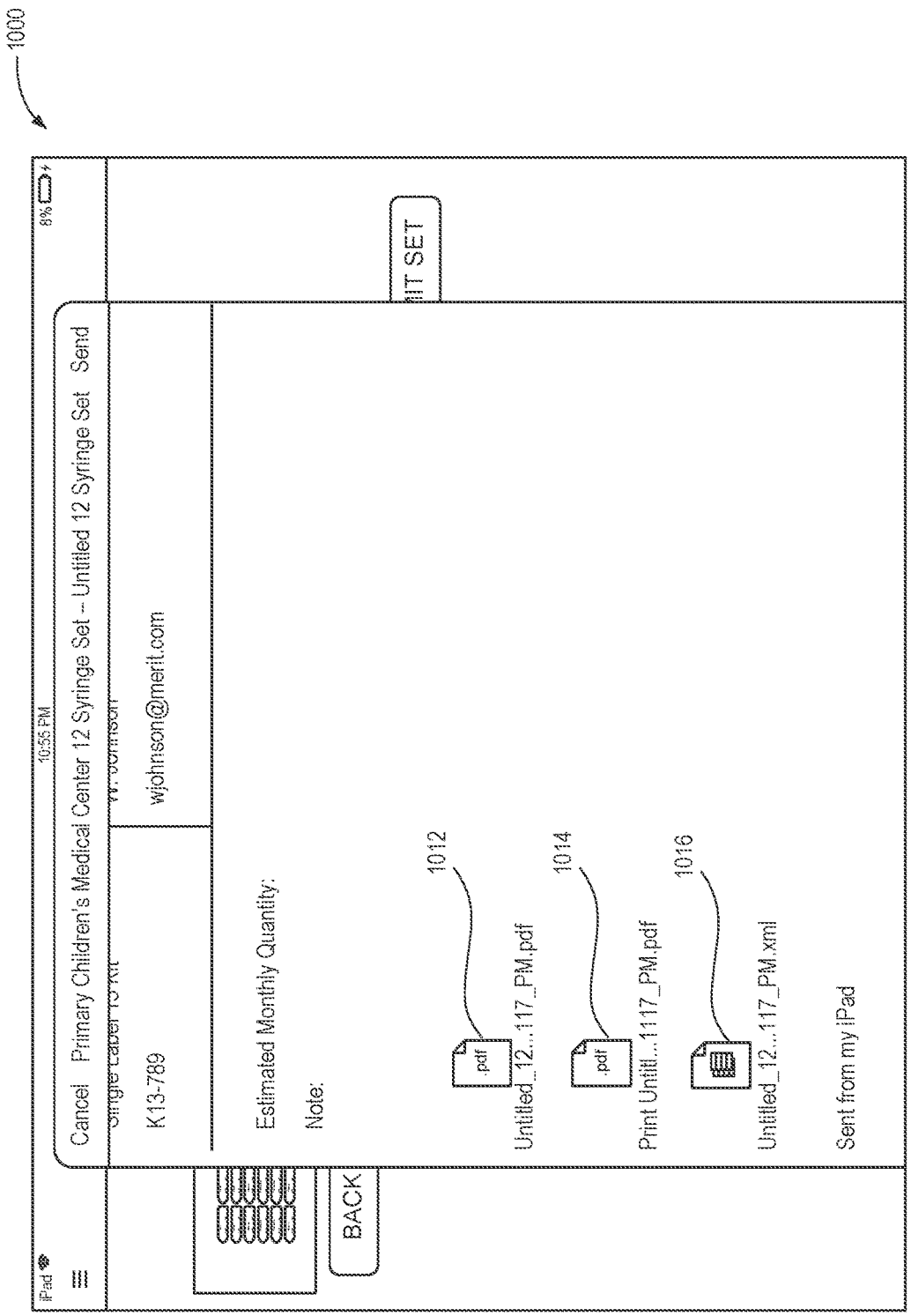

FIGS. 10A and 10B are another user interface 1000 of a medical device customization client computing device, according to one embodiment. The user interface 1000 provides a rendering of a specification file to be transmitted to a medical device customization system. In the illustrated embodiment, the specification file comprises a plurality of separate files 1012, 1014, 1016 and is transmitted via an email to the medical device customization system. The user interface 1000 provides another opportunity for the user to confirm the information being transmitted to the medical device customization system.

Although the foregoing user interfaces illustrated in the figures are directed to customized medical grade labels, a person of ordinary skill appreciates that variations of these interfaces may be directed to customized medical kits, and other medical devices having customizable features.

Figure 11:
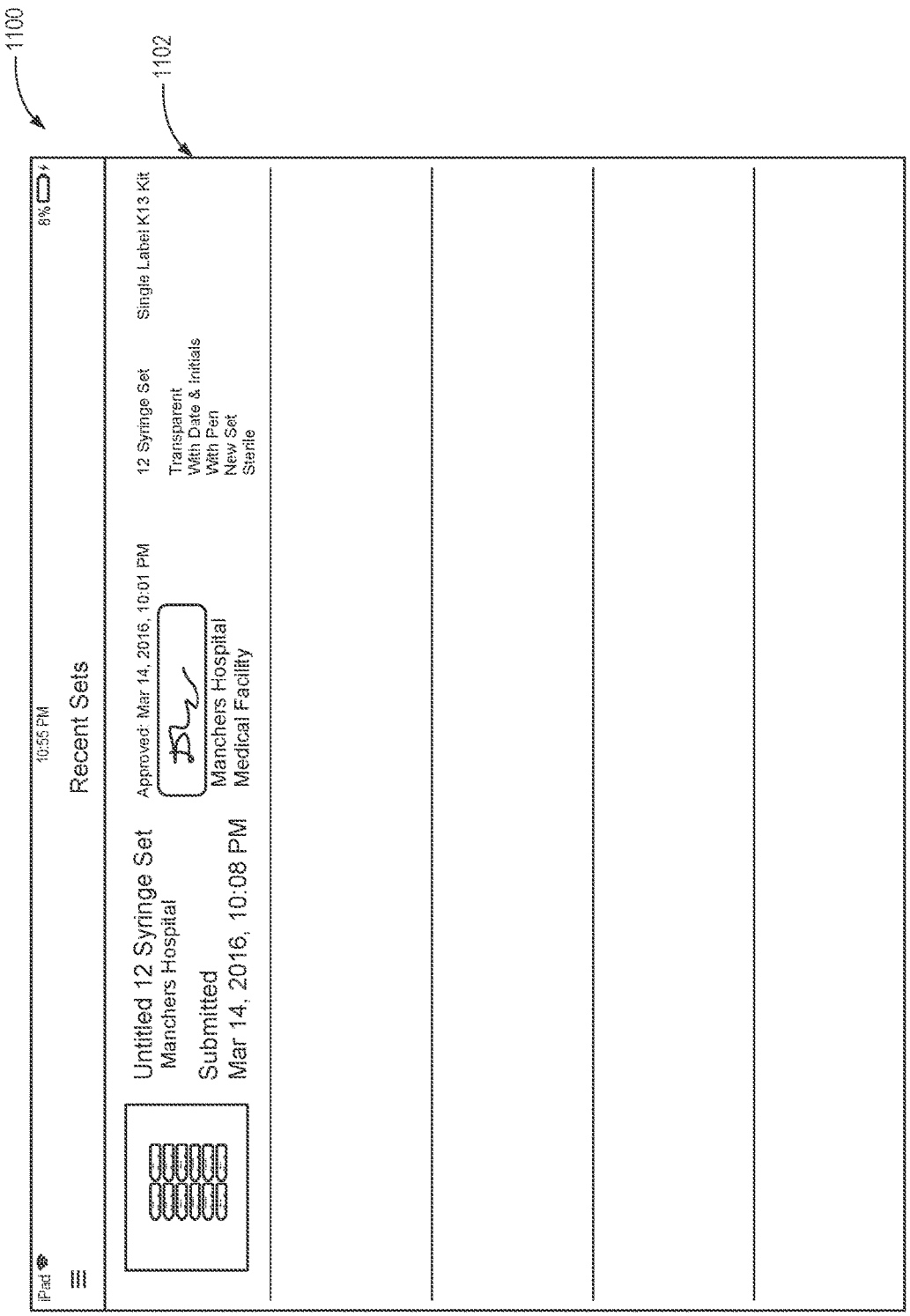
FIG. 11 is another user interface of a medical device customization client computing device, according to one embodiment.

FIG. 11 is another user interface 1100 of a medical device customization client computing device, according to one embodiment. The user interface 1100 presents a listing of one or more past orders 1102 of customized medical devices. The user interface 1100 may enable revisions of previously customized medical devices from a past order 1102. The user interface 1100 may also provide ability to manage past orders 1102, revise past orders (e.g., to create new customizations), or duplicate past orders for the same customer or for another customer.

FIG. 12 is another user interface 1200 of a medical device customization client computing device, according to one embodiment. The user interface 1200 presents a listing 1204 of one or more customers 1214 for which past orders of customized medical devices have been placed. The user interface 1200 presents a record of past orders according to customer. The user interface 1200 may enable a user to manage past orders 1202 for a given customer, including revise past orders (e.g., to create new customizations) or duplicate past orders of a customer.

Figure 13:
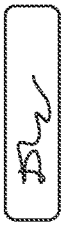
FIG. 13 is another view of the interface of FIG. 12.

FIG. 13 is the user interface 1200 of FIG. 12 with the listing 1204 expanded to show passed orders 1302a, 1302b (individually or collectively 1302) of a selected customer 1214. A user can select (e.g., tap, double-tap/-click) a customer 1214 entry in the listing 1200 and the user interface 1200 presents an expanded view reflecting the orders 1302 that customer 1214 may have placed in a past recent period of time. The user interface also provides an edit input component 1313 that can be manipulated to enable editing of customer information and/or order information of orders associated with the customer. The user interface 1200 presents a record of past orders 1302, according to customer. The user interface 1200 may enable a user to manage past orders 1202 for a given customer, including revise past orders (e.g., to create new customizations) or duplicate past orders of a customer.

Figure 14:
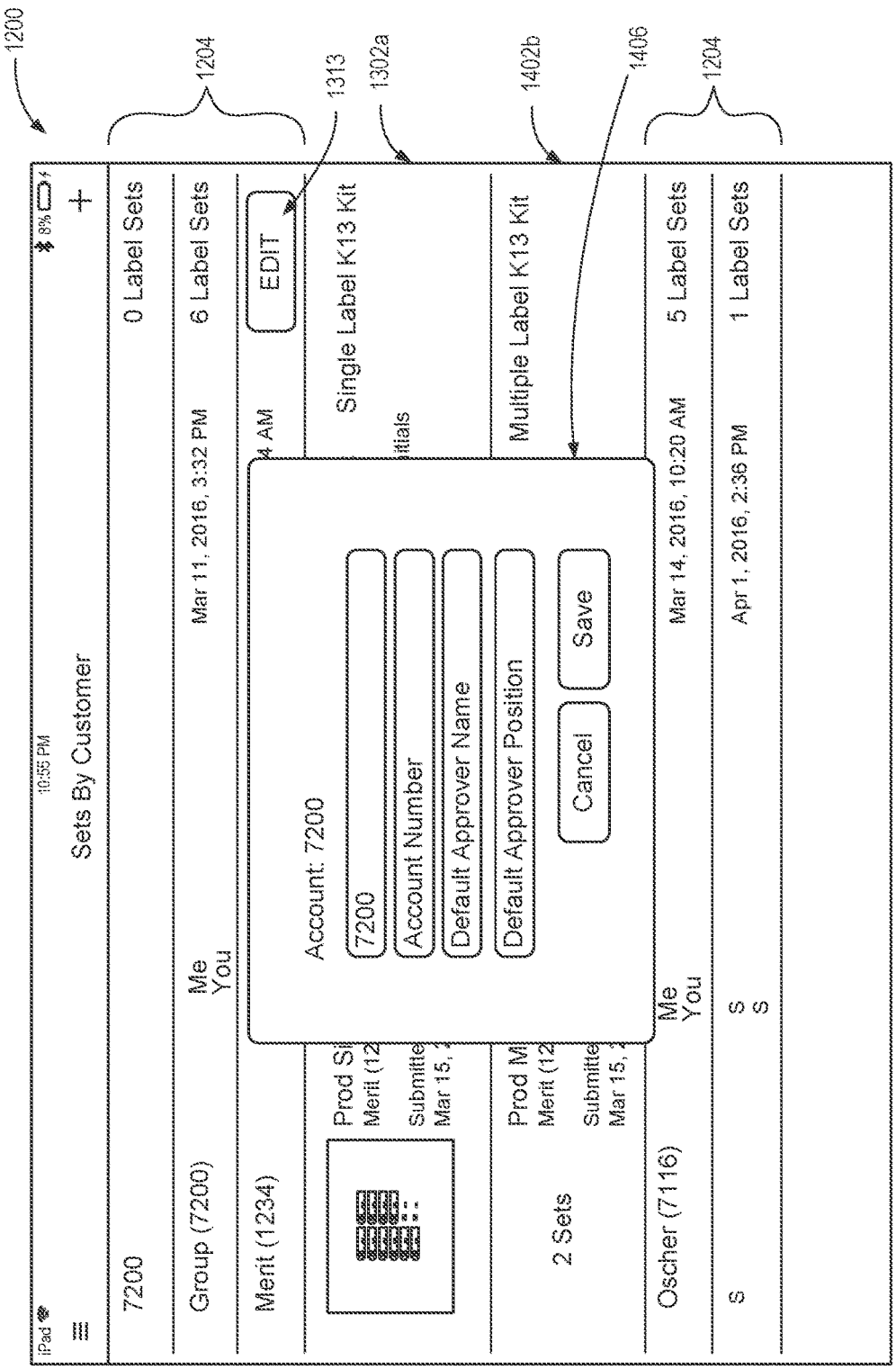
FIG. 14 is another view of the interface of FIG. 12.

FIG. 14 is the user interface 1200 of FIG. 12 including a pop-up input component 1406 that enables user input to change customer information. The pop-up input component 1406 may be presented by the user interface 1200 in response to manipulation of the edit input component 1313. The pop-up input component 1406 may enable a user to input such information as an account name, account number, approver name, approver position to set this information with respect to all future, pending, and/or past orders for the given customer.

Figure 15:
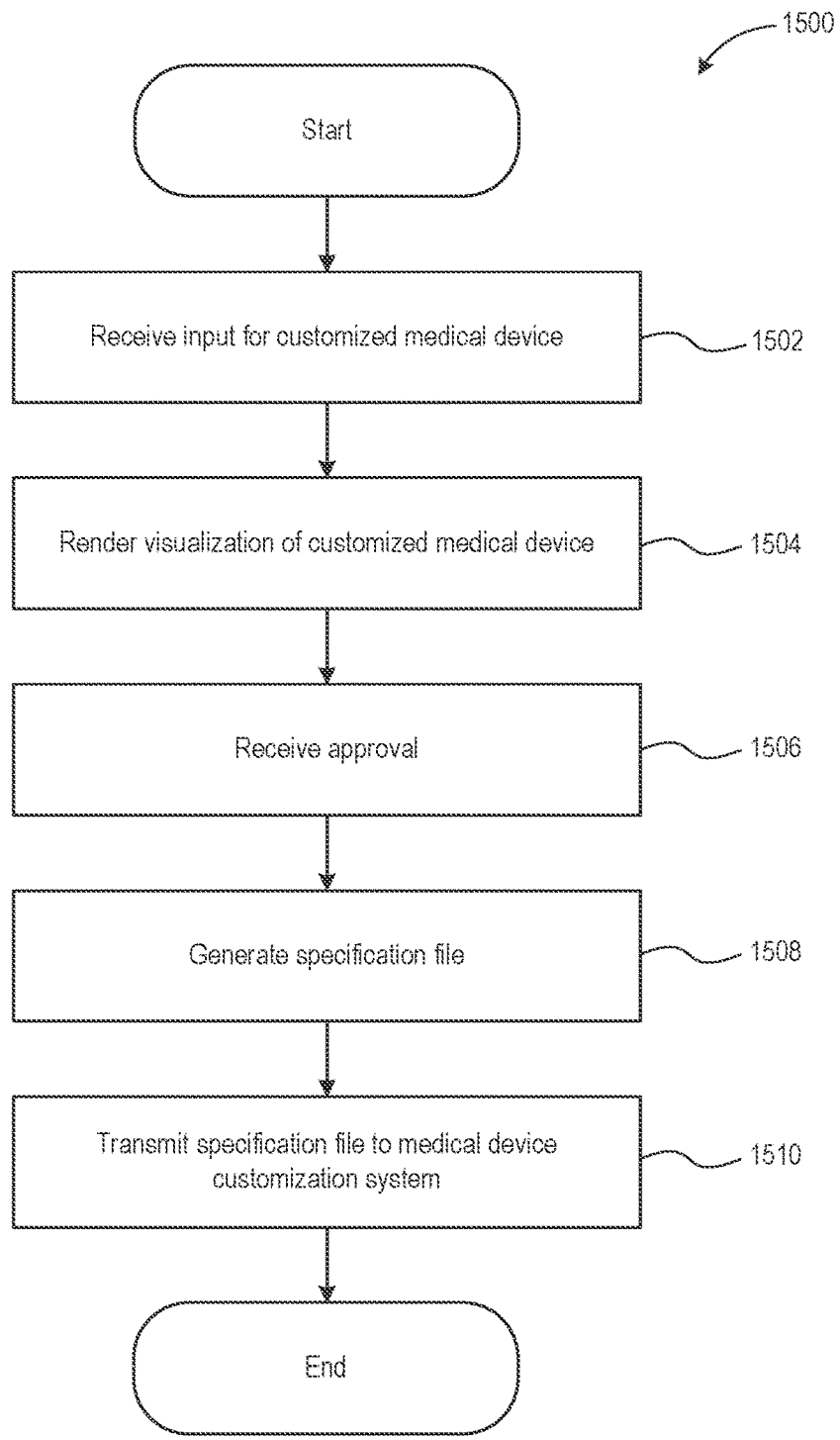
FIG. 15 is a flow diagram of a method for producing medical devices, according to one embodiment.

FIG. 15 is a flow diagram 1500 of a method for producing medical devices, according to one embodiment. Input for a customized medical device is received 1502, such as at a client computing device. The input may include input indicating the medical device and customization of one or more features of the medical device that produce the customized medical device. A visualization or representation of the customized medical device may be rendered 1504, such as for user review and/or approval. Approval is received 1506, such as via the client computing device, and a specification file is generated 1508 and then transmitted 1510 to a medical device customization system.

Figure 16:
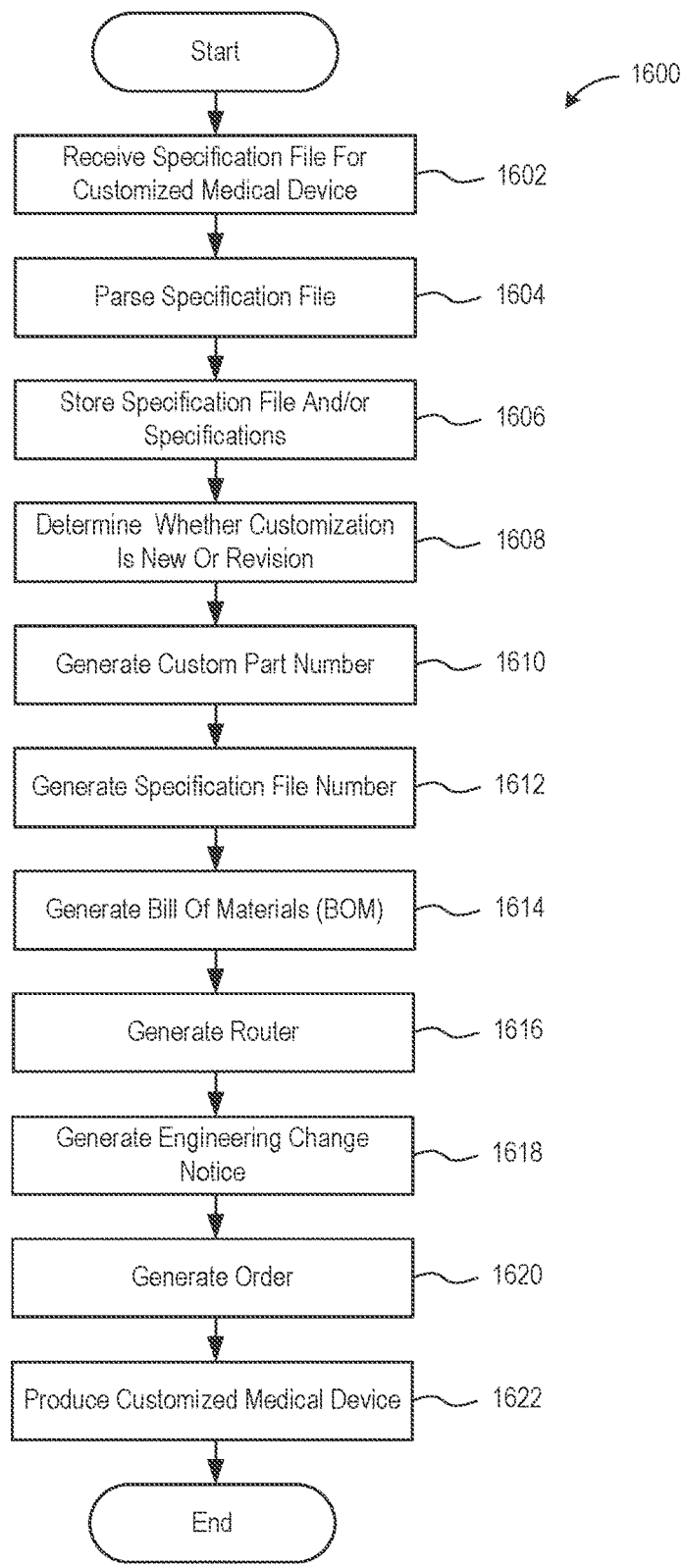
FIG. 16 is a flow diagram of a method for producing medical devices, according to another embodiment.

FIG. 16 is a flow diagram 1600 of a method for producing medical devices, according to another embodiment. A specification file is received 1602 that provides specifications for customization of a medical device. The specifications may specify a medical device and customization of one or more features of the medical device for a customized medical device. The specification file may be received 1602 at a central processing computing device, such as a medical device customization system (e.g., the medical device customization system 200 of FIG. 2). The specification file may be parsed 1604 to determine the specifications, and the specification file and/or the specifications are stored 1606 in an electronic storage medium accessible by the central processing computing system.

A determination may be made 1608 whether the customization (e.g., the customization of the medical device to produce the customized medical device) is new or a revision of an existing customization.

A custom part number may be generated 1610, such as by the central processing computing system. The custom part number is generated for the customized medical device and can be unique to the customized medical device and to a customer placing an order for the customized medical device.

A specification file number may be generated 1612 to identify the specification file and/or the set of specifications parsed from the specification file.

A manufacturing order (e.g., a purchase order or work order) and/or one or more manufacturing documents may be generated as follows.

A bill of materials (BOM) can be generated 1614 by the central processing computing system based on the specification file. The BOM provides a listing of materials to produce the customized medical device.

A router can be generated 1616 by the central processing computing system. The router can be generated 1616 based on, or otherwise using, the specification file. The router provides instructions for assembling or otherwise manufacturing the customized medical device according to the specification file and/or specifications.

An engineering change notice (ECN) can be generated 1618 by the central processing computing system to associate the specification file, the BOM, and the router. The ECN may be delivered to an automated process and/or a manual process to provide quality assurance and/or approval to assemble and/or otherwise manufacture the customized medical device. The ECN, including the specification file, the BOM, and the router, may be communicated to an engineering function.

The manufacturing order (e.g., a purchase order or work order) can be generated 1620 for transmittal to a manufacturing system. The manufacturing system may be local to (or internal to an organization of) the central processing computing system. The manufacturing system may also be a third-party system, external to an organization of the central processing computing system. The manufacturing order provides all the manufacturing documents needed by the manufacturing system to produce 1622 the customized medical device. The manufacturing system can produce 1622 the customized medical device according to the specification file, using the materials provided by the listing of materials of the bill of materials, by following the instructions for assembling the customized medical device provided by the router.

As can be appreciated, other embodiments may include additional steps or may arrange the foregoing steps in a different order.

The foregoing specification has been described with reference to various embodiments, including the best mode. However, those skilled in the art appreciate that various modifications and changes can be made without departing from the scope of the present disclosure and the underlying principles of the invention. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

As used herein, the terms "comprises," "comprising," and any other variation thereof are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Principles of the present disclosure may be reflected in a computer program product on a tangible computer-readable storage medium having computer-readable program code means embodied in the storage medium. Any suitable computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture including instruction means which implement the function specified. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified.

Principles of the present disclosure may be reflected in a computer program implemented as one or more software modules. As used herein, a software module or component (e.g., an engine) may include any type of computer instruction or computer-executable code located within a memory device and/or computer-readable storage medium. A software module may, for instance, comprise one or more physical or logical blocks of computer instructions, which may be organized as a routine, a program, an object, a component, a data structure, etc. that perform one or more tasks or implement particular data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools.

Embodiments as disclosed herein may be computer-implemented in whole or in part on a digital computer. The digital computer includes a processor performing the required computations. The computer further includes a memory in electronic communication with the processor to store a computer operating system. The computer operating systems may include, but are not limited to, MS-DOS, Windows, Linux, UNIX, AIX, CLIX, QNX, OS/2, and Apple. Alternatively, it is expected that future embodiments will be adapted to execute on other future operating systems.

In some cases, well-known features, structures, or operations are not shown or described in detail. Furthermore, the described features, structures, or operations may be combined in any suitable manner in one or more embodiments. It will also be readily understood that the components of the embodiments as generally described and illustrated in the figures herein could be arranged and designed in a wide variety of different configurations.

Various operational steps, as well as components for carrying out operational steps, may be implemented in alternative ways depending upon the particular application or in consideration of any number of cost functions associated with the operation of the system; e.g., one or more of the steps may be deleted, modified, or combined with other steps.

While the principles of this disclosure have been shown in various embodiments, many modifications of structure, arrangements, proportions, elements, materials, and components, used in practice, which are particularly adapted for a specific environment and operating requirements, may be used without departing from the principles and scope of this disclosure. These and other changes or modifications are intended to be included within the scope of the present disclosure.

The scope of the present invention should, therefore, be determined only by the following claims.

The invention claimed is:

1. A system for producing customized medical devices, comprising:
   one or more processors;
   a memory in electrical communication with the one or more processors to store specifications to produce customized medical devices;
   a network interface to enable communication with one or more computing devices over an electronic communication network;
   a client interface to, by the one or more processors via the network interface, receive a specification file from a client computing device over the electronic communication network, the specification file including a set of specifications that specify a medical device and customization of one or more features of the medical device to produce a customized medical device, wherein at least one of the specification file and the set of specifications are stored in the memory;
   a part number generator to, by the one or more processors, generate a part number for the customized medical device, wherein the part number is unique to the customized medical device, and wherein the part number is unique to a customer placing an order for the customized medical device; and
   an order generator to, by the one or more processors, generate a manufacturing order for producing the customized medical device according to the specification file and to provide the manufacturing order to a manufacturing system,
   wherein the system determines, based on the specification file, whether the customized medical device is a new customization or a revision of an existing customization, wherein
   if the customized medical device is a revision of an existing customization, the manufacturing order to produce the customized medical device is transmitted to a manual manufacturing system, and
   if the customized medical device is a new customization, the manufacturing order to produce the customized medical device is transmitted to an automated manufacturing system.

2. The system of claim 1, wherein the order generator comprises:
   a manufacturing documentation generator to, by the one or more processors, generate one or more manufacturing documents to enable a manufacturing system to produce the customized medical device according to the specification file, wherein the manufacturing order includes the one or more manufacturing documents.

3. The system of claim 2, wherein the manufacturing documentation generator comprises:
   a bill of materials generator to, by the one or more processors, generate a bill of materials based on the specification file, the bill of materials providing a listing of materials to produce the customized medical device; and
   a router generator to, by the one or more processors, generate a router based on the specification file, the router providing instructions for assembling the customized medical device.

4. The system of claim 3, wherein the order generator comprises:
   an engineering change notice generator to, by the one or more processors, generate an engineering change notice to associate the specification file, the bill of materials, and the router and to, by the one or more processors, provide the engineering change notice, the specification file, the bill of materials, and the router to an engineering system for review and approval to produce the manufacturing order.

5. The system of claim 3, wherein the customized medical device comprises a plurality of polymer components as provided in the listing of materials of the bill of materials, the polymer components assembled together using the instructions provided by the router for assembling the customized medical device.

6. The system of claim 1, wherein the order generator comprises:
an engineering change notice generator to, by the one or more processors, generate and provide an engineering change notice to an engineering system for review and approval to produce the manufacturing order.

7. The system of claim 1, wherein the manufacturing order to produce the customized medical device includes a purchase order to be provided to a third-party manufacturing system.

8. The system of claim 1, wherein the manufacturing order to produce the customized medical device is a work order to be provided to an internal manufacturing system.

9. The system of claim 1, wherein the manufacturing system comprises a printing system to print customized medical grade labels.

10. The system of claim 1, further comprising a parsing engine to, by the one or more processors, parse the specification file received from the client computing device, wherein the parsing engine parses from the specification file the set of specifications that specify the medical device and customization of the one or more features of the medical device to produce the customized medical device, and stores the set of specifications to the memory.

11. The system of claim 1, further comprising a customer service interface to, by the one or more processors, communicate the part number to a customer service system.

12. The system of claim 1, wherein the medical device is a set of one or more medical grade labels.

13. The system of claim 1, wherein the customized medical device is a kit including a medical grade label that is biocompatible and a pen having ink that marks on the label and maintains integrity on the label in the presence of liquid.

14. The system of claim 1, wherein the client interface provides to the client computing device a graphical user interface for presentation on the client computing device, the graphical user interface to receive option input to configure one or more specifications in the set of specifications and to communicate the option input to the client interface.

15. A method for producing a customized medical device, comprising:
receiving, at a central processing computing system from a client computing device, a specification file that provides a set of specifications that specify one or more features for a customized medical device;
storing, in an electronic storage medium accessible by the central processing computing system, one or more of the specification file and the set of specifications;
generating, by the central processing computing system, a custom part number for the customized medical device, wherein the custom part number is unique to the customized medical device, and wherein the part number is unique to a customer placing an order for the customized medical device;
generating, by the central processing computing system, a bill of materials based on the specification file, the bill of materials providing a listing of materials to produce the customized medical device;
generating, by the central processing computing system, a router based on the specification file, the router providing instructions for producing the customized medical device;
generating, by the central processing computing system, an engineering change notice to associate the specification file, the bill of materials, and the router;
communicating the engineering change notice, the specification file, the bill of materials, and the router to an engineering function;
determining, based on the specification file, whether the customized medical device is a new customization or a revision of an existing customization, wherein
if the customized medical device is a revision of an existing customization, transmitting the engineering change notice, the specification file, the bill of materials, and the router to a manual manufacturing system, and
if the customized medical device is a new customization, transmitting the the engineering change notice, the specification file, the bill of materials, and the router to an automated manufacturing system; and
producing the customized medical device according to the specification file, using the materials provided by the listing of materials of the bill of materials, and following the instructions for producing the customized medical device provided by the router.

16. The method of claim 15, wherein the medical device is a set of one or more medical grade labels, wherein each label in the set of one or more medical grade labels is biocompatible.

17. The method of claim 15, wherein the medical device is a kit including a medical grade label that is biocompatible and a pen having ink that marks on the label and maintains integrity on the label in the presence of liquid.

18. The method of claim 15, wherein the medical device comprises a plurality of polymer components as provided in the listing of materials of the bill of materials, the polymer components assembled together using the instructions provided by the router for assembling the customized medical device.

19. The method of claim 15, further comprising:
parsing, by the central processing computing system, the specification file to determine the set of specifications to produce the customized medical device.

20. The method of claim 15, further comprising:
determining, at the central processing computing system, based on the specification file, whether the customized medical device is a new customization or a revision of an existing customization.

21. The method of claim 15, further comprising:
receiving, at the client computing device, option input indicating a medical device and customization of one or more features of the medical device for producing the customized medical device;
rendering on the client computing device a representation of the customized medical device;
generating, by the client computing device, the specification file providing the specifications for the customized medical device; and
transmitting the specification file to the central processing computing system over an electronic communication network.

* * * * *